(12) United States Patent
Martin et al.

(10) Patent No.: US 10,912,674 B2
(45) Date of Patent: Feb. 9, 2021

(54) VISCOELASTIC APPLICATOR FOR IOL INSERTION APPARATUS

(71) Applicant: JOHNSON & JOHNSON SURGICAL VISION, INC., Santa Ana, CA (US)

(72) Inventors: Nicholas E. Martin, Newport Beach, CA (US); Renee Van Dorne, Mission Viejo, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 265 days.

(21) Appl. No.: 16/194,191

(22) Filed: Nov. 16, 2018

(65) Prior Publication Data

US 2019/0083309 A1 Mar. 21, 2019

Related U.S. Application Data

(60) Continuation of application No. 14/979,361, filed on Dec. 22, 2015, now abandoned, which is a division of
(Continued)

(51) Int. Cl.
*A61F 9/007* (2006.01)
*A61F 2/16* (2006.01)
*B23P 19/04* (2006.01)

(52) U.S. Cl.
CPC ........ *A61F 9/00736* (2013.01); *A61F 2/1664* (2013.01); *A61F 2/1678* (2013.01); *B23P 19/04* (2013.01); *Y10T 29/49826* (2015.01)

(58) Field of Classification Search
CPC .... A61F 2/1678; A61F 2/1691; A61F 2/1675; A61F 2/1672; A61F 2/167; A61F 2/1667; A61F 2/1662
See application file for complete search history.

(56) References Cited

U.S. PATENT DOCUMENTS 6,093,193 A 7/2000 Makker et al.
6,203,549 B1 3/2001 Waldock
(Continued)

FOREIGN PATENT DOCUMENTS

EP 1481652 A1 12/2004
EP 1800623 A1 6/2007
(Continued)

OTHER PUBLICATIONS

International Search Report and Written Opinion, dated Oct. 1, 2008, and International Preliminary Report on Patentability, dated Jan. 19, 2010, for Application No. PCT/US2008/070200, 8 pages.

*Primary Examiner* — Thomas McEvoy
(74) *Attorney, Agent, or Firm* — Johnson & Johnson Surgical Vision, Inc.

(57) ABSTRACT

A system for preparing an intraocular lens (IOL) injector for receipt of an IOL. A manifold mates with an injector cartridge and easily distributes a lubricating agent to a load chamber of the cartridge. The IOL is then transferred into the load chamber. The cartridge may be rotatably coupled to the handpiece, and then converted from a preparation and load position to a delivery position. The manifold may remain external to the load chamber or fit within the load chamber and include a handle that remains outside. One or more internal channels in the manifold lead from one or more inlet ports to surfaces in the load chamber than contact the IOL.

20 Claims, 8 Drawing Sheets

Related U.S. Application Data application No. 13/790,345, filed on Mar. 8, 2013, now Pat. No. 9,220,592, which is a division of application No. 11/779,217, filed on Jul. 17, 2007, now Pat. No. 8,398,651.

(56) References Cited

U.S. PATENT DOCUMENTS

| | | |
|---|---|---|
| 2002/0022881 A1 | 2/2002 | Figueroa et al. |
| 2004/0160575 A1 | 8/2004 | Ayton et al. |
| 2004/0243141 A1 | 12/2004 | Brown et al. |
| 2005/0049605 A1 | 3/2005 | Vaquero et al. |
| 2006/0052796 A1 | 3/2006 | Perez et al. |
| 2006/0064112 A1 | 3/2006 | Perez |
| 2006/0184181 A1 | 8/2006 | Cole et al. |
| 2008/0027460 A1 | 1/2008 | Kobayashi |
| 2008/0039862 A1 | 2/2008 | Tran |

FOREIGN PATENT DOCUMENTS

| | | |
|---|---|---|
| WO | 0164147 A1 | 9/2001 |
| WO | 05030097 A1 | 4/2005 |
| WO | 06070219 A1 | 7/2006 |

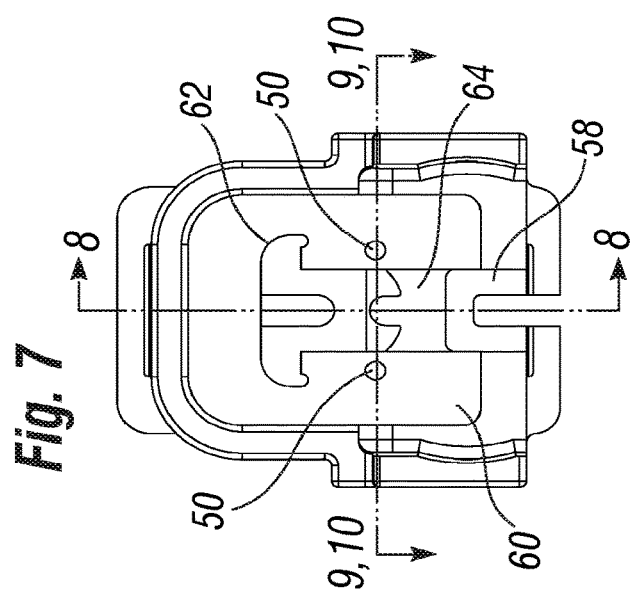
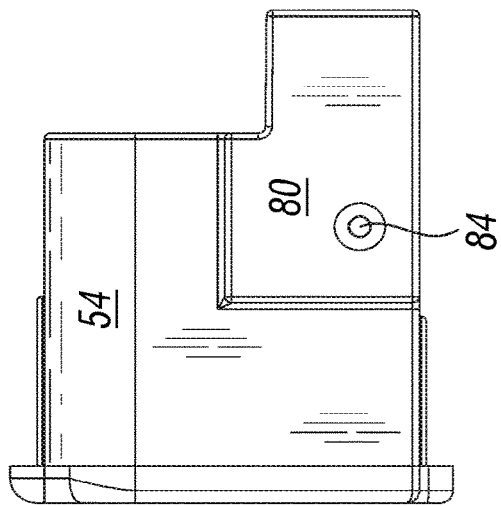
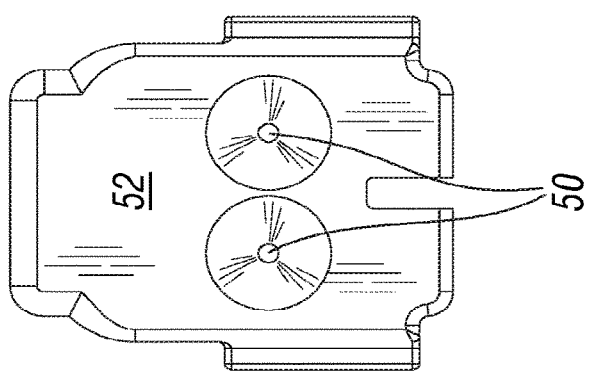
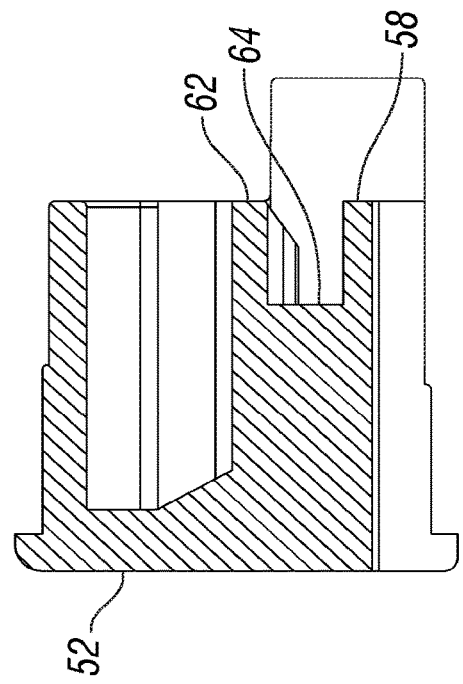

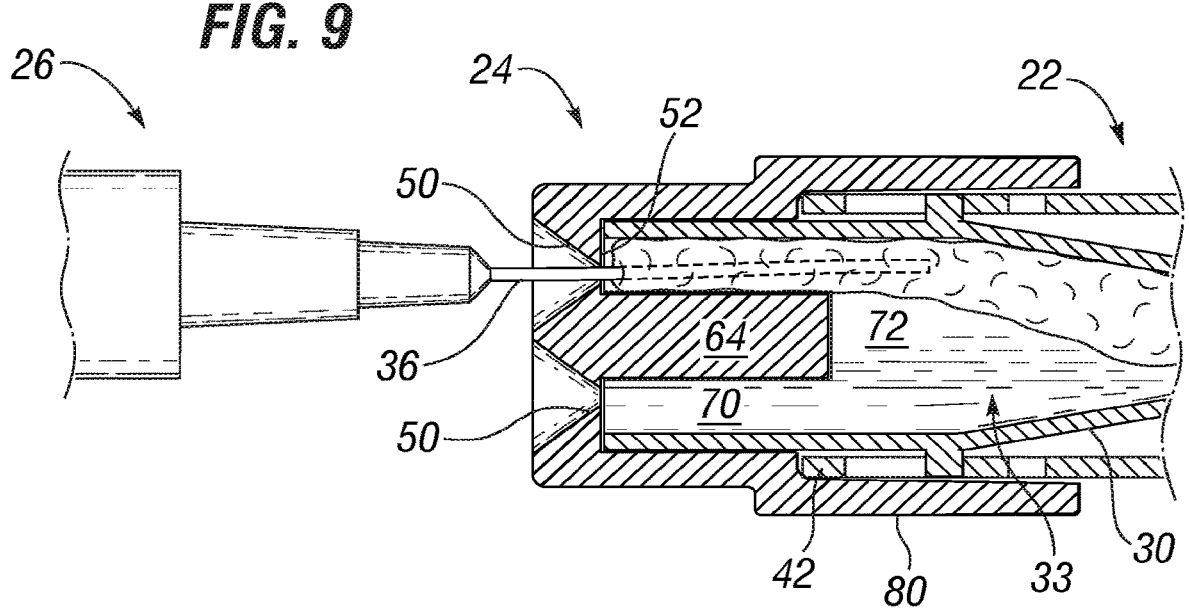
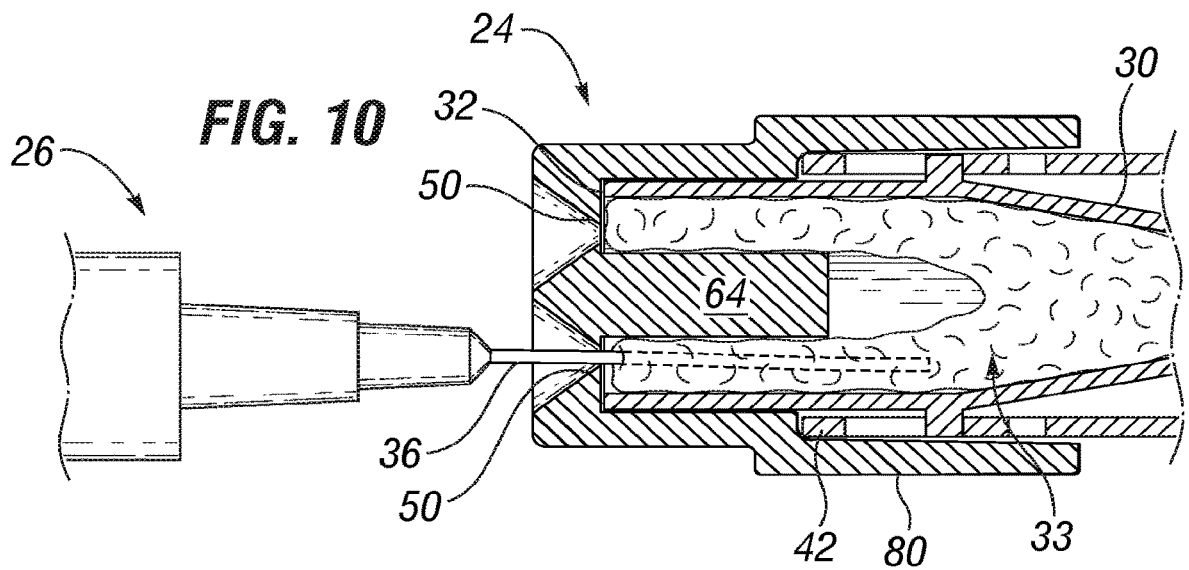

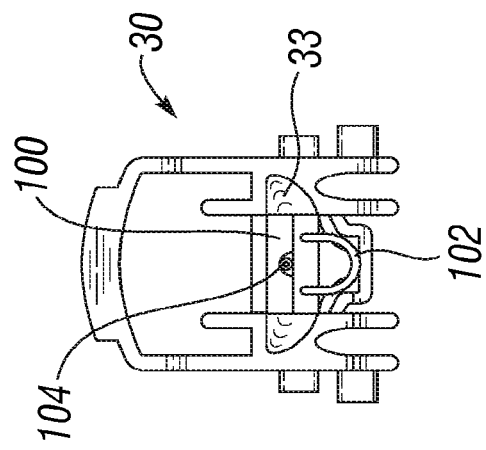
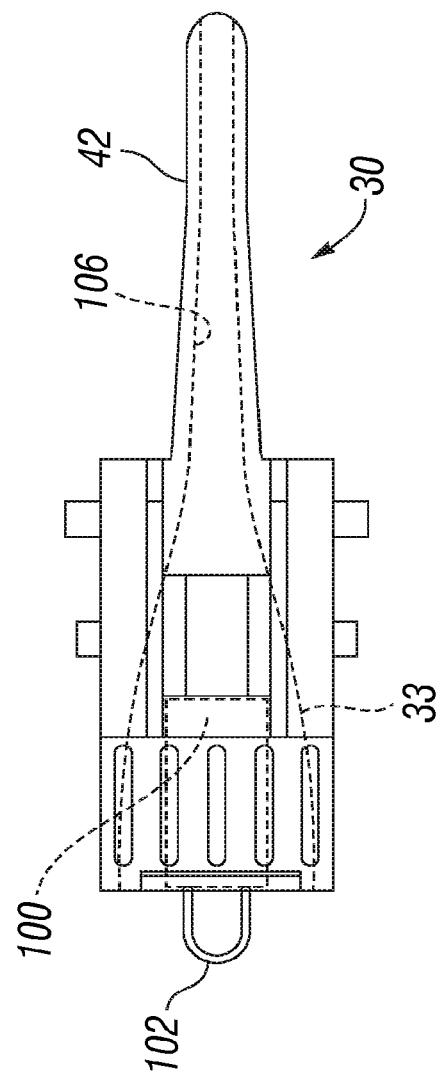

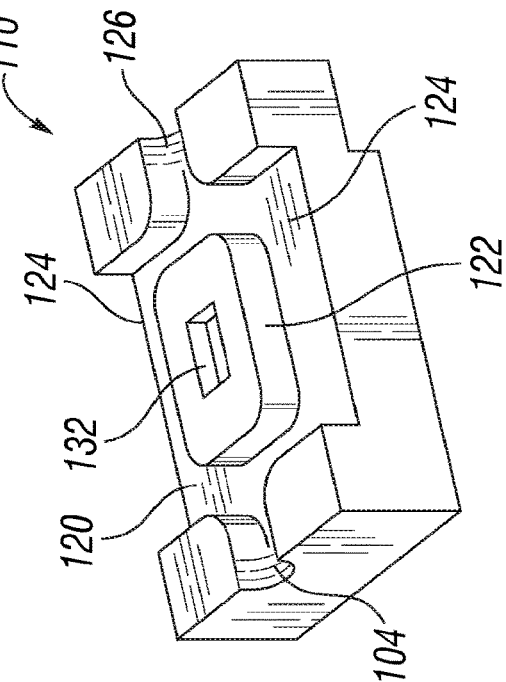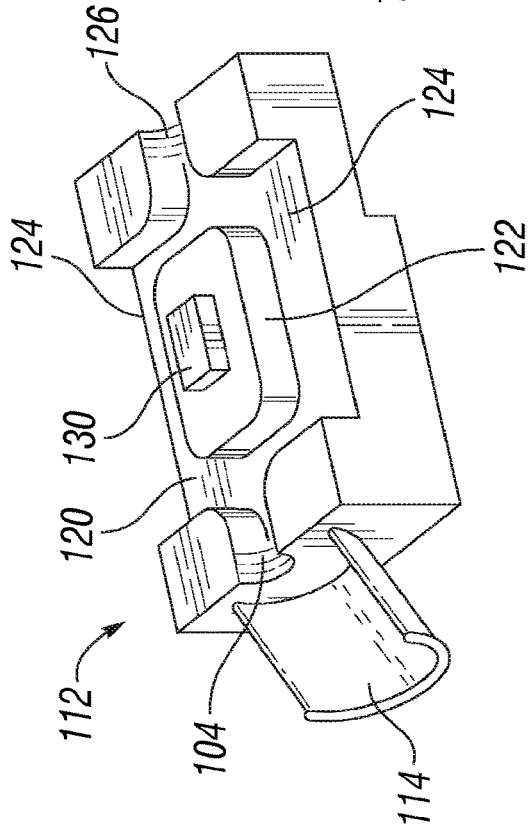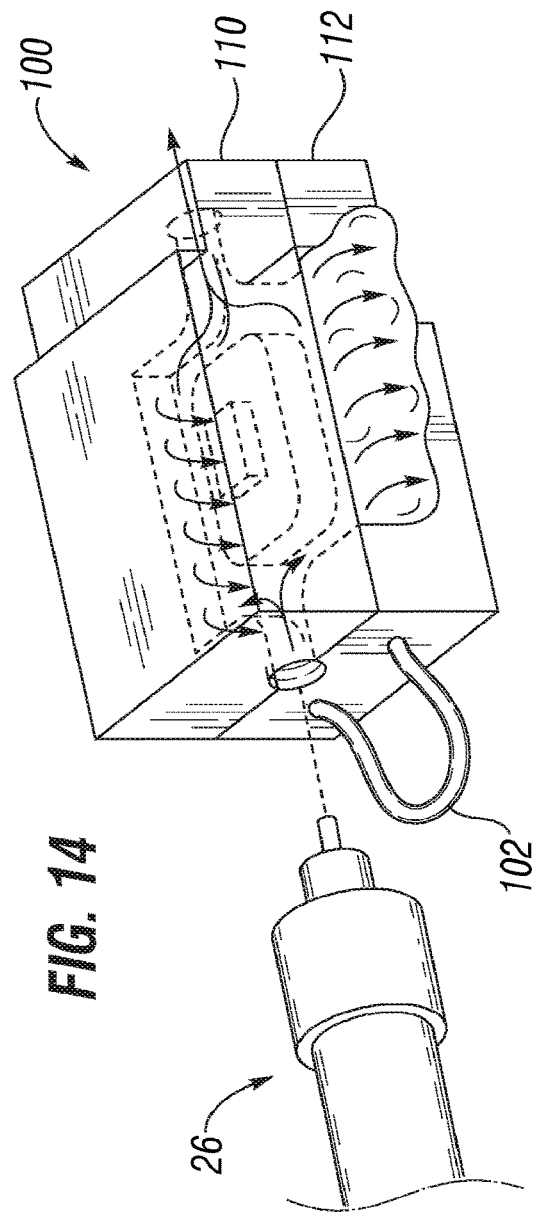

VISCOELASTIC APPLICATOR FOR IOL INSERTION APPARATUS

RELATED APPLICATIONS

This application is a continuation application of, and claims priority to, U.S. application Ser. No. 14/979,361 filed on Dec. 22, 2015, which is a divisional application of, and claims priority to, U.S. application Ser. No. 13/790,345 filed on Mar. 8, 2013, now U.S. Pat. No. 9,220,592, which is a divisional application of, and claims priority to, U.S. application Ser. No. 11/779,217 filed on Jul. 17, 2007, now U.S. Pat. No. 8,398,651, the entire contents of which are hereby incorporated by reference in its entirety for all purposes as if fully set forth herein.

FIELD OF THE INVENTION

The present invention relates to devices, systems, and methods for preparing an injector for delivering an intraocular lens (IOL) into an eye. More particularly, the invention relates to devices and methods for applying a lubricating agent to an IOL injector.

BACKGROUND OF THE INVENTION

Intraocular lenses (IOLs) may be implanted in the eye of a subject to replace the natural crystalline lens or to otherwise modify the vision of an eye containing either the natural lens or another IOL. IOLs commonly include an optic and one or more flexible fixation members or haptics extending from the optic to secure and center the optic within the eye. When the IOL replaces the natural lens, the natural lens must first be removed, for instance, using a phacoemulsification system. The IOL is then generally implanted using an insertion apparatus or device that rolls, folds, or otherwise configures the lens for delivery through a small incision in the eye in a way that reduces trauma and expedites post-surgery healing.

Injectors for delivering IOLs into the eye typically employ a handpiece and a cartridge having a hollow insertion tube or cannula through which the folded IOL is passed using a pushrod. The cartridges are made of disposable materials, such as plastics, and remain in a sterile package until ready for coupling with the handpiece. Some injectors do without the cartridge and are reusable. The pushrod and insertion tube may be designed to advantageously provide the surgeon precise control of the IOL as it is placed inside the eye, for example as disclosed in U.S. Pat. No. 6,093,193, herein incorporated by reference. The IOL is stored separately and transferred to a load chamber in the injector or cartridge just prior to delivery. Typically, the load chamber is first partially filled with a liquid or gel, for example, a viscoelastic medium or "Ophthalmic Viscosurgical Device" (OVD). The lubricating viscoelastic facilitates passage of the IOL through the injector, and in some cases the tip of the pushrod does not directly contact the IOL, but instead engages the intermediate viscoelastic so as to distribute hydraulic pressure across the IOL and cause it to proceed through the injector and into the eye.

One viscoelastic substance used is sodium hyaluronate sold under the trade name Healon®, though Balanced Salt Solutions (BSS) and other lubricating agents are used. In the context of the present invention, a "lubricating agent" encompasses all of these choices. These substances are sold preloaded in a syringe, typically provided with a thin cannula tip. The process of applying the viscoelastic to the relatively tiny inner surfaces of the injector in the operating room just prior to surgery can be difficult and time-consuming.

It would be advantageous to provide an improved way to apply the lubricating agent to an injector during an ocular surgery that is easy and quick.

SUMMARY OF THE INVENTION

The exemplary IOL delivery system includes a fluid manifold adapted to mate with the IOL injector or cartridge, the manifold having at least one inlet port leading to internal channels such that a lubricating agent injected into the inlet port is guided by the internal channels into the injector load chamber.

One embodiment of the invention is a system for delivering an intraocular lens (IOL) into the eye of a subject, comprising an IOL injector defining an insertion tube and a load chamber for receiving an IOL. The injector also includes a pushrod movable through the load chamber for urging the IOL from the load chamber and through the insertion tube in a delivery procedure. A fluid manifold is formed to mate with the injector and has at least one inlet port that when mated with the injector leads to the load chamber. Lubricating agent injected into the inlet port is automatically guided onto surfaces within the load chamber that will contact the IOL.

The fluid manifold may remain external to the load chamber or fit within the load chamber when mated with the injector. If internal, the fluid manifold includes a handle that remains external to the injector when the manifold resides in the load chamber. The load chamber desirably has at least two spaced surfaces that contact the IOL, and the fluid manifold includes at least two separate inlet ports each leading to a different spaced surface. In one version, the fluid manifold includes at least two internal channels and the two inlet ports each lead to a separate internal channel. Alternatively, the load chamber has at least two spaced surfaces that contact the IOL, and the fluid manifold includes at least two internal channels and only one inlet port that communicates with the two internal channels.

The injector preferably includes a handpiece coupled to a cartridge defining the load chamber, and the cartridge is movable relative to the handpiece between a first position for loading the intraocular lens and a second position for delivering the intraocular lens into the subject's eye. For instance, a transfer interface of the cartridge open to the load chamber faces away from the handpiece in the first position, and the insertion tube faces away from the handpiece in the second position, the fluid manifold being formed to mate against the transfer interface of the cartridge in the first position. In one embodiment the cartridge rotates 180° about the handpiece between the first and second positions.

Another aspect of the invention is a method for preparing an intraocular lens (IOL) injector for receiving an IOL. The method includes providing an IOL injector defining an insertion tube open to a load chamber for receiving an IOL, and a fluid manifold formed to mate with the injector and having at least one inlet port. The fluid manifold mates with the cartridge, and a lubricating agent is injected into the inlet port so that the manifold automatically guides the lubricating agent onto surfaces within the load chamber that will contact the IOL.

The injector may have a handpiece coupled to a cartridge defining the load chamber, and the method may further including placing the cartridge in a first position relative to the handpiece for mating with the fluid manifold, and then moving the cartridge into a second position relative to the handpiece after disengaging the fluid manifold for delivering the IOL into a subject's eye. Desirably, the insertion tube is defined on the cartridge and the cartridge rotates 180° about the handpiece between the first and second positions, wherein a transfer interface of the cartridge faces away from the handpiece in the first position and the insertion tube faces away from handpiece in the second position, the fluid manifold being formed to mate against the transfer interface of the cartridge in the first position. Or, the fluid manifold is formed to insert into the load chamber through the transfer interface of the cartridge in the first position. The fluid manifold may remain external to the load chamber or fit within the load chamber when mated with the injector. The fluid manifold and injector preferably include complementary structural features that positively engage with audible or tactile feedback when the manifold and injector mate to indicate full engagement.

BRIEF DESCRIPTION OF THE DRAWINGS

Embodiments of the present invention will be better understood from the following detailed description when read in conjunction with the accompanying drawings. Such embodiments, which are for illustrative purposes only, depict the novel and non-obvious aspects of the invention. The drawings include the following figures, with like numerals generally indicating like parts:

FIGS. 5-8 are elevational and sectional views of the fluid manifold;

FIGS. 9 and 10 are sectional views through the assembled insertion system of FIG. 1 showing the application of a lubricating agent using the fluid manifold;

FIGS. 11 and 12 are top and end views of an IOL injector cartridge with an alternative internal fluid manifold therein for guiding lubricating agent to appropriate IOL-contacting surfaces;

FIGS. 13A and 13B are bottom and top halves, respectively, of one version of the internal fluid manifold of FIGS. 11 and 12;

FIG. 14 is an assembled view of the manifold halves of FIGS. 13A and 13B;

DETAILED DESCRIPTION OF THE PREFERRED EMBODIMENTS

The present invention facilitates the process of delivering an intraocular lens (IOL) into a patient's eye using an injector. The IOL is typically implanted using an injector that rolls, folds, or otherwise configures the lens for delivery through a small incision in the eye in a way that reduces trauma and expedites post-surgery healing. The IOL is stored separately and transferred to an injector or cartridge just prior to delivery. The injector or injector/cartridge is used in a manner like a hypodermic needle with the IOL being injected into the eye through a delivery tube. The injector is first partially filled with a liquid or gel lubricating agent, for example a viscoelastic material. The present invention provides a guide or fluid manifold that couples to the injector and facilitates introduction of a lubricating agent into a load chamber of the injector or cartridge. Desirably, the manifold is packaged with the cartridge or separately, and the IOL in its case is also packaged separately. These two components plus the reusable injector and lubricating agent are all that is required for the procedure, other than the standard operating room implements.

Figure 1:
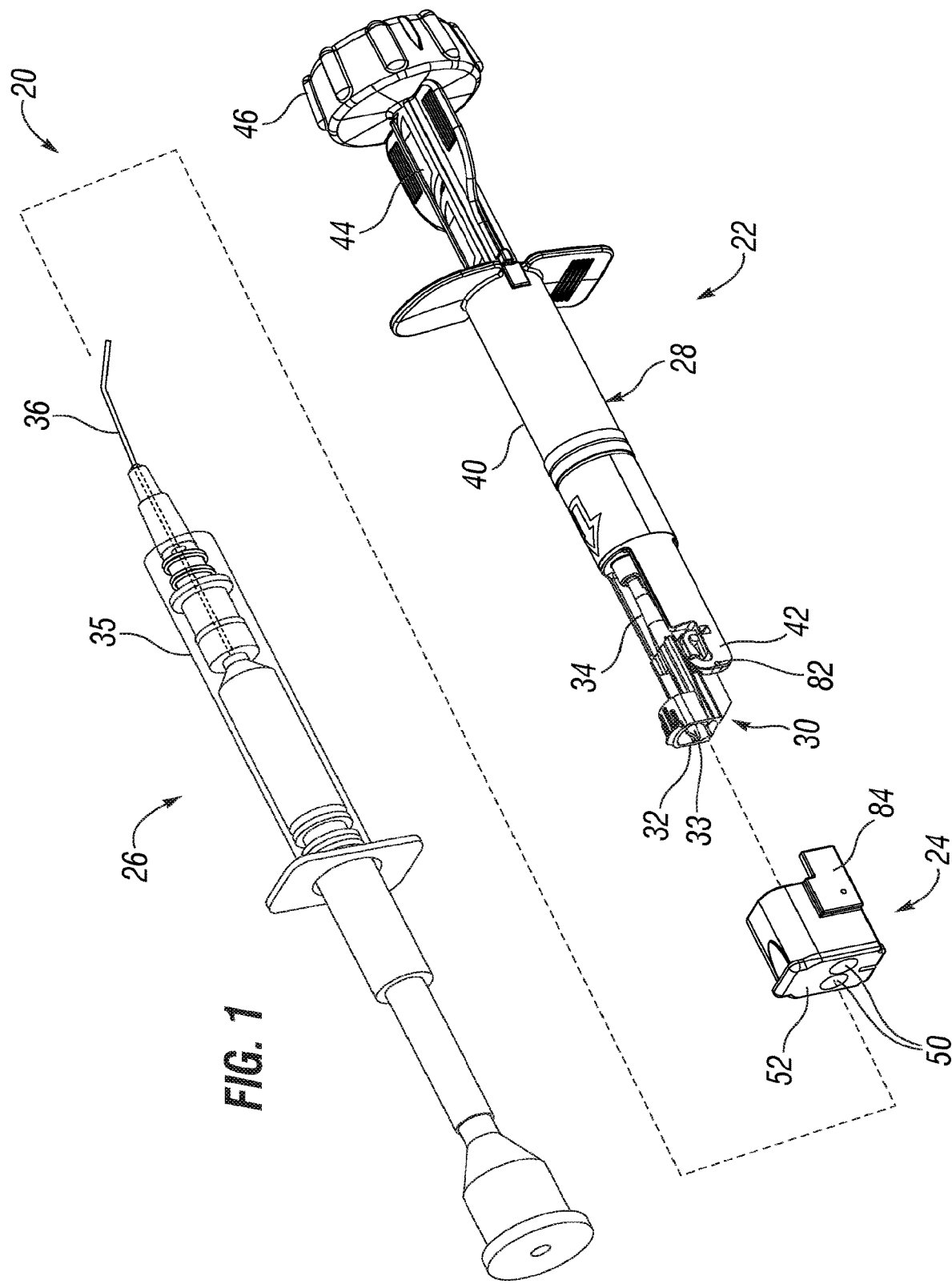
FIG. 1 is a perspective exploded view of an exemplary insertion system according to an embodiment of the invention showing an injector, a viscoelastic applicator, and a fluid manifold therebetween.
Figure 2:
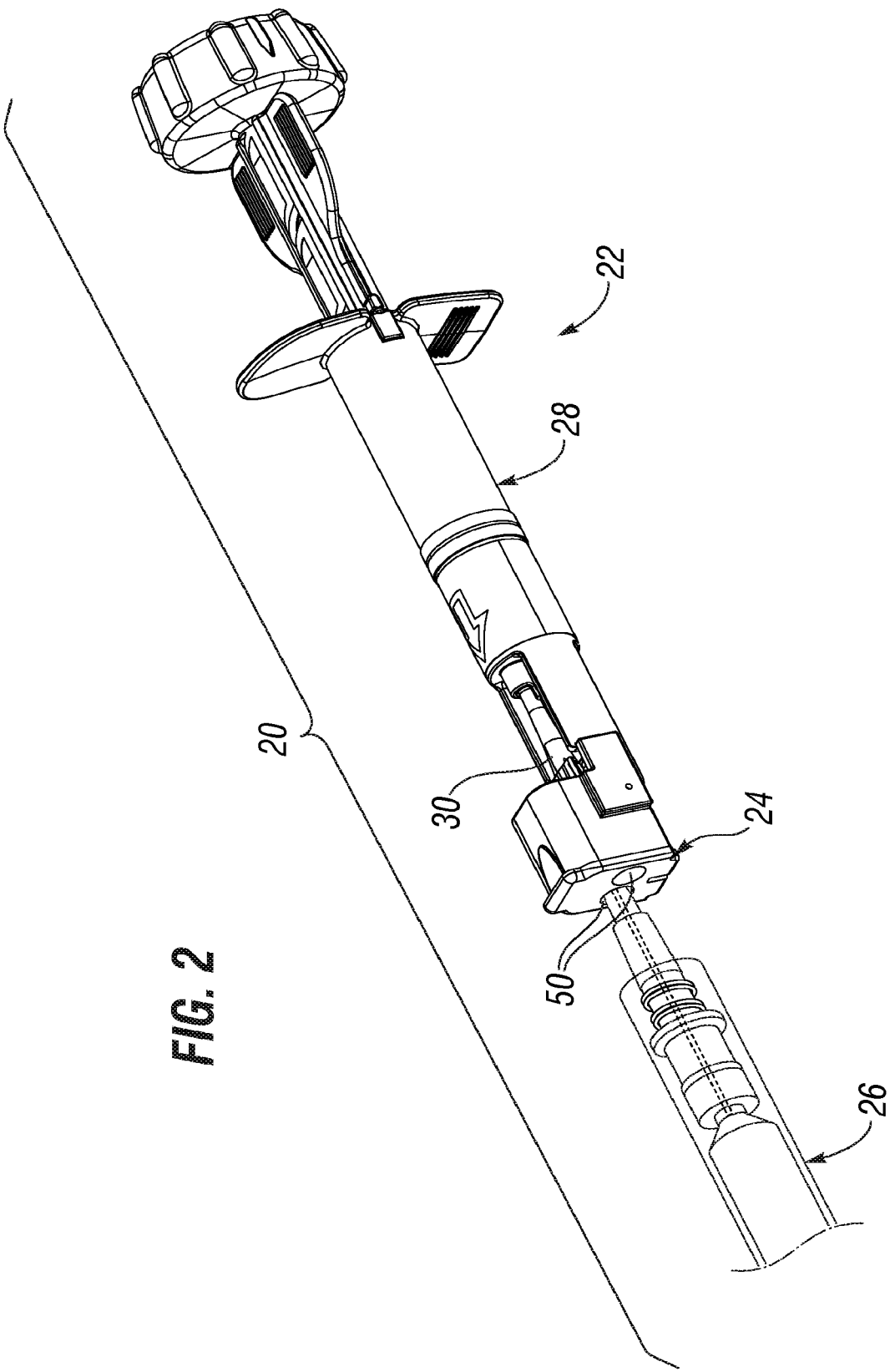
FIG. 2 is a perspective view of the assembled insertion system of FIG. 1.

FIGS. 1 and 2 are perspective exploded and assembled views, respectively, of an insertion system 20 according to an embodiment of the invention. The insertion system 20 comprises an injector 22, a fluid guide or manifold 24, and a viscoelastic applicator 26. The exemplary injector 22 includes a handpiece 28 coupled to a distal nosepiece or cartridge 30, seen in an IOL transfer mode. In this mode, the cartridge 30 is in a position to receive an IOL (not shown) through a transfer interface 32. The cartridge 30 defines a cavity or load chamber 33 within for receiving the IOL, and also has an insertion tube 34 extending in the opposite direction than the transfer interface 32. A continuous path exists through the length of the cartridge 30 from the transfer interface 32, load chamber, and insertion tube 34.

In one embodiment, disclosed in U.S. Patent Publication 2006/0184181, the injector 22 engages a case that contains an IOL, whereupon the IOL is automatically transferred to the cartridge 30. The IOL case in U.S. Patent Publication 2006/0184181 has a transfer port configured to couple to the transfer interface of the cartridge and used during transfer of the IOL from the case to the load chamber 33. Alternatively, the IOL could be transferred manually into the cartridge 30. Prior to transfer of the IOL into the cartridge 30, however, a lubricating agent will be introduced into the cartridge, and more particularly into a load chamber therein, as will be explained below.

One exemplary viscoelastic applicator 26 is sold as the Healon® viscoelastic applicator by Advanced Medical Optics (AMO), Inc. of Santa Ana, Calif. The applicator 26 includes a syringe-like body 35 on the distal end of which is connected a thin cannula 36. The viscous medium within the body 35 may be expelled through the cannula 36, enabling good control of the precise location of delivery. However, IOL cartridges are quite small and the surfaces that require lubrication intricate, which makes the task of priming the cartridge quite intensive. Again, lubricating agents other than viscoelastics are utilized, including Balanced Salt Solutions (BSS), and in the context of the present invention the viscoelastic applicator 26 is representative of lubricating agent applicators in general.

It should be understood that the present invention contemplates a manifold that serves as an intermediary between the injector or cartridge and a lubricating agent applicator to facilitate and speed up the process of applying the lubricating agent to the load chamber. In this respect, various kinds of injectors and cartridges are known, and manifolds that adapt to those designs are included in the scope of the invention. For example, a common injector cartridge includes a hinged polymer structure in which the IOL is placed, originally termed a Bartell-style cartridge after its inventor. Folding the structure causes the IOL to fold as well, much like a taco. Such a system is primed first with the lubricating agent, such as using the applicator 26 shown in FIG. 1. Even though the Bartell-style cartridges are opened wide, the surfaces needing a lubricating agent are many and tiny, so the task remains somewhat labor-intensive. A fluid manifold such as that shown herein may be useful for such cartridges to speed up the delivery preparation process.

Likewise, other IOL delivery systems would benefit from a fluid manifold as described herein, though the structural features of such manifolds would be different than the illustrated manifold 24 herein. Exemplary IOL delivery systems on the market that could use a manifold in accordance with the present invention include the AMO Emerald and Silver Series Unfolders, the Monarch line of Delivery Systems from Alcon Laboratories, Inc. of Fort Worth, Tex., the Mport, Microsert, Passport and SofPort model injectors from Bausch & Lomb (B&L) of Rochester, N.Y., and the MicroSTAAR injectors from STAAR Surgical Company of Monrovia, Calif. It is also important to note again that some of these injectors employ a handpiece and a cartridge while others do without the cartridge, and the manifold mates with either to guide a lubricating agent to the load chamber. Furthermore, various injectors are pre-loaded wherein the IOL starts out in the load chamber. The present invention also applies to such injectors. Any manifold for use with these various insertion systems will provide at least one inlet port that when mated with the injector leads to the load chamber such that a lubricating agent injected into the inlet port is guided into appropriate surfaces of the load chamber. In this sense, the manifold may be viewed as a guide of sorts for the delivery tips of various lubricating agent applicators.

The illustrated applicator 26 has a relatively long and thin cannula 36 which is guided by the manifold 24 to the proper locations within the cartridge load chamber. Other applicators, such as the B&L OcuCoat® Viscoelastic, may have a somewhat blunter tip which a manifold of the present invention may be configured to receive. Likewise, a manifold adapted to mate with BSS applicators would be useful. In short, there are numerous structural possibilities for the fluid manifolds of the present invention and the scope of the appended claims therefore should not be limited to the illustrated embodiment.

With reference again to FIGS. 1 and 2, the injector handpiece 28 has a proximal end and a distal end to which the cartridge 30 couples. The handpiece 28 includes a generally tubular barrel 40 having a pair of bifurcated brackets 42 on a distal end thereof for retaining the cartridge 30. A plunger 44 translates longitudinally within the barrel 40. The plunger 44 comprises a shaft-like member with a drive cap 46 fixed on a proximal end thereof, and a distal end that engages a pushrod (not shown). Although not shown, the pushrod terminates at its distal end in a bifurcated tip that contacts and urges the IOL from the injector during the implant procedure.

In the illustrated embodiment, the cartridge 30 moves relative to the handpiece from the IOL transfer mode shown in FIG. 1 to a delivery mode, such as by rotating 180° about the brackets 42. The IOL transfer mode defines a first position of the cartridge 30 for loading the IOL in which the transfer interface 32 faces away from the handpiece 28. Although not shown, the delivery mode defines a second position for delivering the IOL into the subject's eye wherein the insertion tube 34 faces away from the handpiece 28 in the second position. Further details of this arrangement are disclosed in U.S. Patent Publication 2006/0184181, which is hereby expressly incorporated by reference.

In the illustrated configuration of injector 22, the lubricating agent is applied when the cartridge 30 is in its first position as shown in FIGS. 1 and 2. The exemplary injector 22 is desirably packaged with the cartridge 30 in the first position. The fluid manifold 24 may be packaged on the end of the injector 22 as shown in FIG. 2, or as a separate item.

The transfer interface 32 presents an opening to the load chamber 33 within the cartridge 30. In this embodiment, the load chamber 33 commences at the transfer interface 32 with a pair of opposed longitudinal grooves for receiving side edges of the optic of the IOL. The fluid manifold 24 is designed to mate closely with the transfer interface 32 and includes a pair of conically recessed inlet ports 50 formed in an outer face 52 leading to internal channels (not shown) within the manifold. The internal channels are shaped and positioned such that a lubricating agent injected into the inlet ports 50 is guided thereby into the appropriate spaces within the load chamber 33. More specifically, the internal channels of the manifold 24 guide the lubricating agent into the two opposed grooves of the load chamber.

Two inlet ports 50 are shown which lead to two internal channels to separately lubricate the longitudinal grooves. However, it is possible to provide just one inlet port which diverges within the manifold 24 toward the separate grooves. FIG. 2 illustrates usage of the viscoelastic applicator 26 to lubricate one of the grooves within the load chamber 33 through one of the inlet ports 50. More details with regard to the internal channels of the fluid manifold 24 will be provided below.

Figure 3:
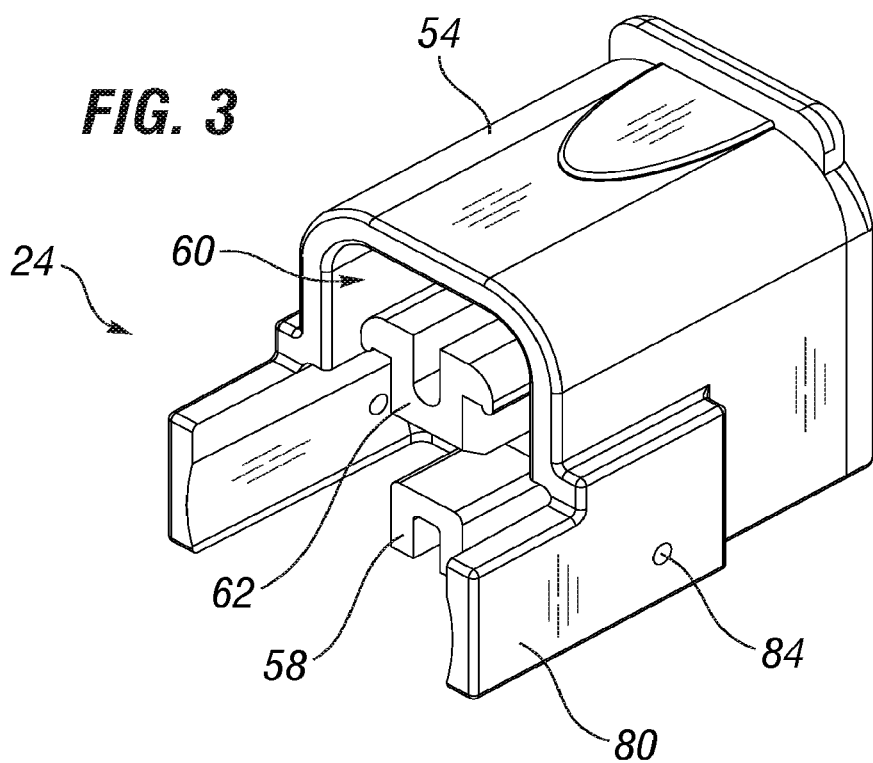
FIGS. 3 and 4 are perspective views of the fluid manifold.
Figure 4:
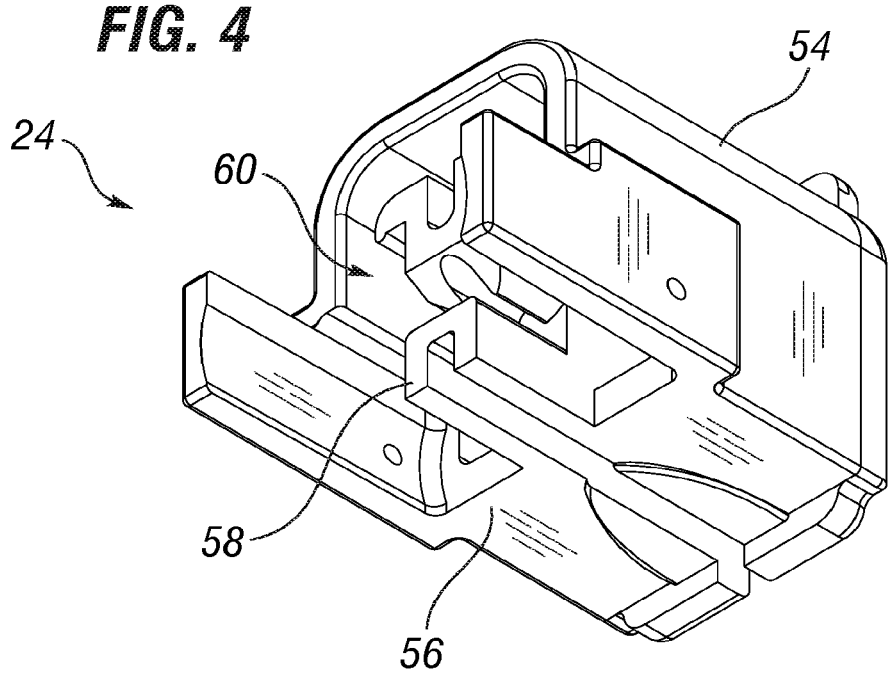

FIGS. 3 and 4 show a preferred embodiment of a fluid manifold 24 for engagement with the exemplary injector 22. The upper and lower perspective views are looking at the manifold 24 from the end opposite the outer face 52 (FIG. 1), which is the end that mates with the injector 22. A three-sided peripheral wall 54 longitudinally projects away from the outer face 52 in an upside down U-shape. A lower wall 56 also projects away from the end wall, though not as far as the peripheral wall 54, and is interrupted by a lower rail 58. The peripheral wall 54 and lower wall 56 together define a generally rectilinear cavity 60 within the manifold 24 that receives and mates with the cartridge 30 of the injector 22.

With reference also to FIGS. 5-8, the manifold 24 defines structure within the cavity 60 that aligns features therein with the transfer interface 32 and load chamber 33 of the cartridge 30. FIG. 5 shows an elevation looking directly at the outer face 52, and the height and spacing of the two conically recessed inlet ports 50. FIG. 7 is an opposite elevation looking directly into the cavity 60 with the inlet ports 50 seen as mere pinholes. As will be seen, when the manifold 24 mates with the cartridge 30, the inlet ports 50 within the cavity 60 align directly with the opposed longitudinal grooves of the load chamber 33.

FIGS. 3-4 and 7 best show a central wall projecting longitudinally from the outer face 52 into the cavity 60. The central wall is formed partly by the lower rail 58, and also by an upper rail 62 and a middle rail 64. The lower and upper rails 58, 62 extend as far as the peripheral wall 54, and the middle rail 64 is recessed therefrom, as also seen in cross-section in FIG. 8. The resulting structure receives the cartridge 30 so that the transfer interface 32 extends fully into the cavity 60 and against the inside of the outer face 52.

Now with reference to FIGS. 9 and 10, mating engagement between the inserter 22 and manifold 24 is shown. As mentioned, the cavity 60 receives the cartridge 30 such that the transfer interface 32 contacts the outer face 52. FIG. 9 shows one of the longitudinal grooves 70 of the load chamber 33 aligned with the lower inlet port 50, while the thin cannula 36 of the viscoelastic applicator 26 projects through the upper inlet port and is shown after having deposited a mass of lubricating agent. Although not further detailed herein, the two longitudinal grooves 70 gradually converge to the right and eventually transition into a tubular delivery channel (not shown) within the insertion tube 34 (FIG. 1). The delivery channel has a distal linear section adjacent its tip and tapers gradually wider toward the load chamber 33. As with other conventional injector cartridges, the tapered delivery channel compresses and forms the IOL into an elongated and/or folded configuration suitable for delivery into the eye. The operator desirably applies lubricating agent along the grooves 70 and at least partway into the tubular delivery channel.

The two longitudinal grooves 70 are separated at the transfer interface 32 and for a distance until joined at a bridge 72. The bridge 72 in this embodiment forms a floor of the load chamber 33, and continues toward the tubular delivery channel. The split nature of the longitudinal grooves 70 is particular to the illustrated cartridge 30, which is designed to engage a case that holds an IOL and receive the IOL therefrom in an automatic process without forceps. In this regard, the inner features of the manifold 24 are specifically designed to accommodate the split grooves 70 and bridge 72. Namely, the lower and upper rails 58, 62 extend past the bridge 72 while the middle rail 64 contacts the bridge as shown. The combined central wall therefore segregates opposite sides of the load chamber 33 for a distance toward the tubular delivery channel, thus ensuring that lubricating agent injected into one of the inlet ports 50 is applied to the corresponding side of the load chamber.

The filling process is seen in FIGS. 9 and 10. Either the fluid manifold 24 arrives mated with the injector 22, or the physician positions it against transfer interface 32, as seen in FIG. 2. The manifold 24 presents the conically-shaped inlet ports 50 into which the technician/physician applies a lubricating agent to the load chamber 33 of the cartridge 30.

First the operator injects lubricating agent into one side of the load chamber 33 as in FIG. 9, and then into the other side as in FIG. 10. Care must be taken to ration about half of the supply of lubricating agent to each side. The conical recesses on the exterior of the inlet ports 50 facilitate entry of the thin cannula 36 as the inlet ports are sized just slightly greater than the cannula. The inlet ports 50 open directly into each side of the load chamber 33, and thus the cannula 36 can easily reach into and apply lubrication along the surfaces that contact the IOL. The process is greatly simplified from the previous difficult task of manually applying the lubricating agent using a syringe and thin cannula to "paint" the relatively tiny inner surfaces of the cartridge.

FIGS. 9 and 10 also illustrate the distal end of the bifurcated brackets 42 of the handpiece 28 that hold the cartridge 30. As seen best in FIGS. 3 and 4, the peripheral wall 54 includes outwardly stepped wings 80 on either side that snap around the brackets 42. Specifically, each bracket 42 features a small bump 82 (FIG. 1) on its exterior that snaps into a like sized hole 84 in the respective wing 80. The brackets 42 extend all the way to the inside end of the wings 80, as seen in FIGS. 9 and 10. In a general sense, the injector 22 and manifold 24 desirably include complementary structural features that positively engage when they mate to indicate full engagement, such as the pin and hole embodiment that produces an audible and tactile click as feedback.

The preceding fluid manifold 24 receives the cartridge 30 and mates against the transfer interface 32 thereon. No part of the manifold 24 extends past the transfer interface 32 into the load chamber 33, although such an extension is not incompatible with the purpose of the manifold. The manifold 24 is thus designed to remain external to the load chamber 33 when fully mated with the injector 22.

In alternative embodiments of the invention, FIGS. 11-16 illustrate several variations of a lubricating agent manifold that fits within the load chamber. FIGS. 11 and 12 show the cartridge 30 from the top and end views with an exemplary internal manifold 100 therein. As seen from the top, the manifold 100 fits partway into the load chamber 33 with only a handle 102 remaining on the outside. FIG. 12 shows the size of the manifold 100 relative to the load chamber 33. Using the handle 102, the operator places the manifold 100 into the load chamber and applies a lubricating agent to an inlet port 104. As will be described in several embodiments below, internal channels in the manifold 100 guide the lubricating agent from the single inlet port 104 to the multiple surfaces within the cartridge 30 that will subsequently contact the IOL. After application of the lubricating agent, the operator removes the manifold 100. FIG. 11 also shows exemplary contours of an internal tubular delivery channel 106 of the cartridge 30 that extends through the insertion tube 34.

FIGS. 13A and 13B show top and bottom manifold halves 110, 112 that can be combined into an internal manifold. FIG. 14 illustrates the internal manifold 100 which may be formed with the top and bottom halves 110, 112, though an alternative handle 114 is seen in FIG. 13A. Specifically, the handle 114 is solid, while the handle 102 is an open loop, but otherwise like parts will be given like numbers.

The top and bottom halves 110, 112 each are formed as a block-shaped member with internal channels 120 on one face. As the reader will see, flipping the top half 110 over onto the bottom half 112 registers the respective internal channels and forms the structure of FIG. 14. Each internal channel 120 commences at the inlet port 104 and diverges around an island 122. The separated channels 120 pass side openings 124 and then converge at an end opening 126. One island 122 has a non-circular pin 130 and the other has a non-circular recess 132 to ensure the halves 110, 112 align and cannot rotate with one another.

FIG. 14 shows the assembled manifold 100 and schematically illustrates the path of lubricating agent therethrough having been injected from an applicator 26. Note that no thin cannula is required as the internal channel 120 directs the single input to the sides and end, corresponding to the longitudinal grooves 70 of the load chamber 33 as well as the delivery channel 106. In this respect the internal manifold 100 provides greater control of the lubricating agent flow than the external manifold 24 described above.

Figure 15A:
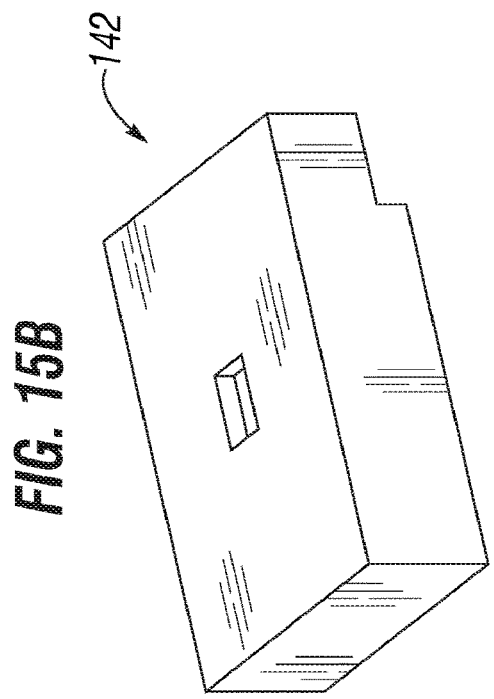
FIGS. 15A and 15B are bottom and top halves, respectively, of another version of the internal fluid manifold of FIGS. 11 and 12.
Figure 15B:
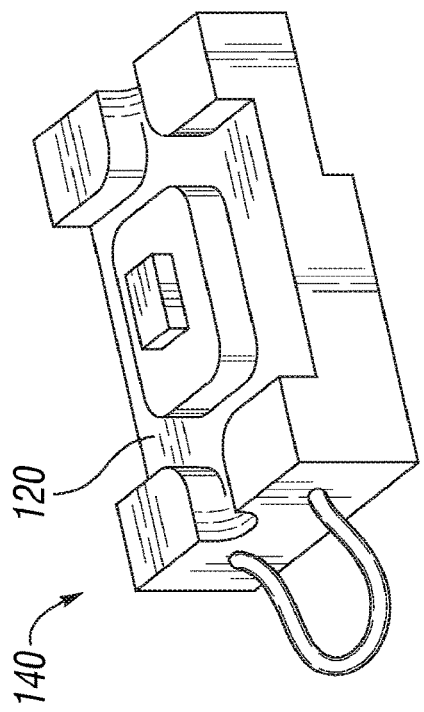
Figure 16:
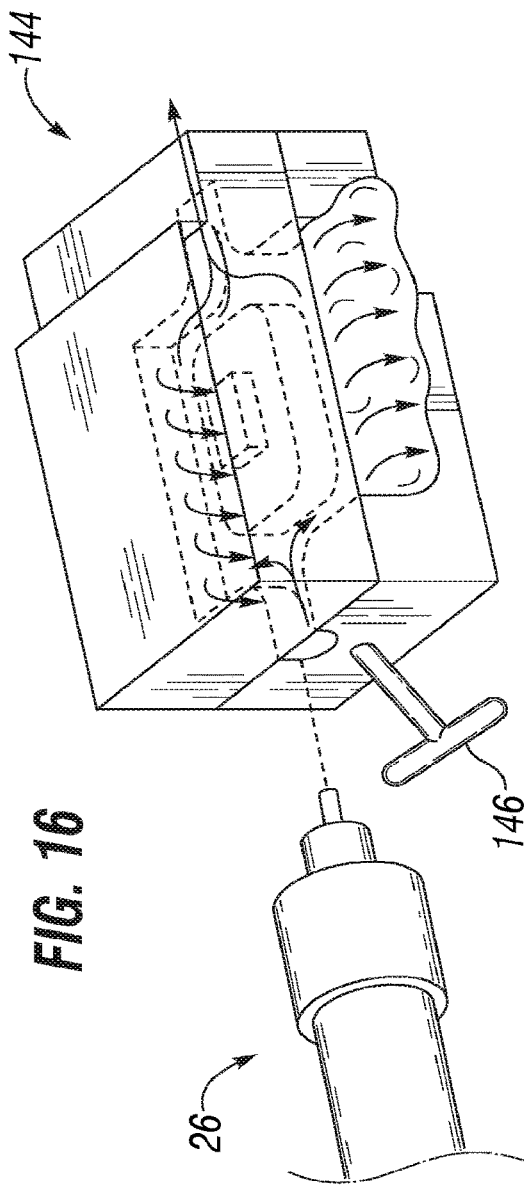
FIG. 16 is an assembled view of the manifold halves of FIGS. 15A and 15B.

FIGS. 15A and 15B illustrate two halves 140, 142 of an alternative manifold 144 of the present invention, assembled with a T-handle 146 in FIG. 16. In this version, the internal channels 120 are only provided on one half, in this case the bottom half 140.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that described above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A system for delivering an intraocular lens (IOL) into the eye of a subject, comprising:

an IOL injector including a handpiece coupled to a cartridge, the cartridge defining an insertion tube and a load chamber for receiving an IOL, the injector further including a pushrod movable through the handpiece and cartridge and into the load chamber for urging the IOL from the load chamber and through the insertion tube in a delivery procedure, wherein the cartridge includes a transfer interface open to the load chamber;

a fluid manifold formed to mate with the transfer interface of the cartridge and having at least one inlet port that when mated with the cartridge leads to the load chamber such that a lubricating agent injected into the inlet port is automatically guided onto surfaces within the load chamber that will contact the IOL, the fluid manifold having internal channels being sized for flow of lubricating agent but are too small for passage of an IOL; and an IOL case configured to hold an IOL and packaged separately from the IOL injector, the case having a transfer port for coupling with the transfer interface and used during transfer of the IOL from the case to the load chamber, wherein the case cannot be coupled to the transfer interface while the fluid manifold is mated therewith.

2. The system of claim 1, wherein the fluid manifold fits within the load chamber when mated with the injector.

3. The system of claim 2, wherein the fluid manifold includes a handle that remains external to the injector when the manifold resides in the load chamber.

4. The system of claim 1, wherein the load chamber has at least two spaced surfaces that contact the IOL, and the fluid manifold includes at least two separate inlet ports each leading to a different spaced surface.

5. The system of claim 4, wherein the fluid manifold includes at least two internal channels and the two inlet ports each lead to a separate internal channel.

6. The system of claim 1, wherein the load chamber has at least two spaced surfaces that contact the IOL, and the fluid manifold includes at least two internal channels and only one inlet port that communicates with the two internal channels.

7. The system of claim 1, wherein the cartridge is movable relative to the handpiece between a first position for loading the intraocular lens and a second position for delivering the intraocular lens into the subject's eye, and wherein the transfer interface faces away from the handpiece in the first position, and the insertion tube faces away from the handpiece in the second position, the fluid manifold being formed to insert into the load chamber through the transfer interface of the cartridge in the first position.

8. The system of claim 7, wherein the cartridge rotates 180° about the handpiece between the first and second positions.

9. The system of claim 1, wherein the internal channels lead from the one inlet port to a pair of lateral openings on opposite sides of the fluid manifold.

10. The system of claim 1, wherein the fluid manifold has top and bottom mating halves between which the internal channels are formed.

11. The system of claim 10, wherein each of the top and bottom mating halves has portions of the internal channels formed on one face that together form the internal channels.

12. The system of claim 10, wherein one of the top and bottom mating halves has a non-circular pin and the other of the top and bottom mating halves has a non-circular recess that receives the pin to ensure the halves align and cannot rotate relative to one another.

13. A system for delivering an intraocular lens (IOL) into the eye of a subject, comprising:

an IOL injector including a handpiece coupled to a cartridge, the cartridge defining an insertion tube and a load chamber for receiving an IOL, the injector further including a pushrod movable through the handpiece and cartridge and into the load chamber for urging the IOL from the load chamber and through the insertion tube in a delivery procedure, wherein the cartridge is movable relative to the handpiece between a first position for loading the intraocular lens and a second position for delivering the IOL into the subject's eye, and wherein a transfer interface of the cartridge open to the load chamber faces away from the handpiece in the first position;

a fluid manifold formed to insert through the transfer interface of the cartridge and into the load chamber with only a handle of the fluid manifold remaining on the outside, the fluid manifold having at least one inlet port and internal channels such that when the fluid manifold is inserted into the load chamber the internal channels lead to the load chamber and a lubricating agent injected into the inlet port is automatically guided onto surfaces within the load chamber that will contact the IOL, the internal channels being sized for flow of lubricating agent but are too small for passage of an IOL; and an IOL case configured to hold an IOL and packaged separately from the IOL injector, the case having a transfer port for transfer of the IOL from the case to the load chamber.

14. The system of claim 13, wherein the cartridge rotates 180° about the handpiece between the first and second positions so that the insertion tube faces away from the handpiece in the second position.

15. The system of claim 13, wherein the handle is selected from the group consisting of an open loop, a solid member and a T shape.

16. The system of claim 13, wherein the internal channels lead from the one inlet port to a pair of lateral openings on opposite sides of the fluid manifold.

17. The system of claim 16, wherein the internal channels further lead to an end opening opposite the inlet port.

18. The system of claim 13, wherein the fluid manifold has top and bottom mating halves between which the internal channels are formed.

19. The system of claim 18, wherein each of the top and bottom mating halves has portions of the internal channels formed on one face that together form the internal channels.

20. The system of claim 18, wherein a first one of the top and bottom mating halves has a non-circular pin and a second one of the top and bottom mating halves has a non-circular recess that receives the pin to ensure the halves align and cannot rotate relative to one another.

* * * * *